United States Patent [19]
Brown

[11] Patent Number: 6,015,389
[45] Date of Patent: Jan. 18, 2000

[54] IMPEDANCE PNEUMOGRAPHY

[75] Inventor: Brian Hilton Brown, Sheffield, United Kingdom

[73] Assignee: BTG International Limited, London, United Kingdom

[21] Appl. No.: 09/090,997

[22] Filed: Jun. 5, 1998

Related U.S. Application Data

[63] Continuation of application No. PCT/GB96/03013, Dec. 5, 1996.

[30] Foreign Application Priority Data

Dec. 6, 1995 [GB] United Kingdom ............... 9524968

[51] Int. Cl.[7] .............................................. A61B 1/00
[52] U.S. Cl. ......................... 600/533; 600/536; 600/529
[58] Field of Search .................................. 600/533–536, 600/372, 529, 300, 301; 606/41; 607/115

[56] References Cited

U.S. PATENT DOCUMENTS

| | | | |
|---|---|---|---|
| 3,608,542 | 9/1971 | Pacela et al. | 600/536 |
| 3,608,543 | 9/1971 | Longini et al. | 600/536 |
| 3,677,261 | 7/1972 | Day | 600/536 |
| 3,871,359 | 3/1975 | Pacela | 600/547 |
| 4,269,195 | 5/1981 | Itoh | 600/536 |
| 4,422,458 | 12/1983 | Kravath | 600/484 |
| 4,708,146 | 11/1987 | Lane | 600/536 |
| 5,170,794 | 12/1992 | Reiche | 600/484 |
| 5,282,840 | 2/1994 | Hudrlik | 600/28 |

FOREIGN PATENT DOCUMENTS

| | | |
|---|---|---|
| 2 272 526 | 5/1994 | United Kingdom . |
| 83 04369 | 12/1983 | WIPO . |
| 86 03391 | 6/1986 | WIPO . |

OTHER PUBLICATIONS

IEEE Transactions on Biomedical Engineering, vol. 42 No. 10, Oct. 1995, New York US.pp. 1044–1048, XP000556838 J. Rosell et al.: "Reduction of motion Artifacts Using a Two_frequency Impedance Plethysmograph and adaptice Filtering" cited in the application see the whole document.
Proceedings of the Annual International Conference of the IEEE Engineering in Medicine and Biology Society, vol. 15, No. 1, Oct. 28–31, 1993, San Diego 100–101, XP000436675 M.B. Gokgoz et al.: "Enhancement of Tissue Contrast in Multifrequency E.I.T." see whole document.

Primary Examiner—Max Hindenburg
Assistant Examiner—Navin Natnithithadha
Attorney, Agent, or Firm—Nixon & Vanderhye

[57] ABSTRACT

The invention concerns a method and apparatus for monitoring respiratory condition by impedance pneumography.

An electrical signal is applied at a plurality of frequencies to a human subject by way of a first pair of spaced electrodes applied to the trunk of the body, whilst the resulting electrical signal is monitored at the plurality of frequencies at different points on the body by way of a second pair of spaced electrodes. From the resulting electrical signal a measure of the impedance of a part of the body at the plurality of frequencies is obtained, and a difference signal representing the impedance change with frequency is calculated. The difference signal is normalized with respect to a signal representative of the impedance measure itself at one or more frequencies, thereby suppressing the effect of those impedance signal components—such as movement artifact—whose frequency dependent change is substantially proportional to the impedance signal value.

The invention improves the reliability of impedance pneumography, especially when employed in situations in which it is difficult to restrict subject movement, such as during sleep. It has particular application in neonatal and infant sleep apnea detection systems.

17 Claims, 5 Drawing Sheets

IMPEDANCE PNEUMOGRAPHY

This application is a continuation of PCT application PCT/GB96/03013, filed Dec. 5, 1996.

The present invention relates to impedance pneumography and, more specifically, to a method and apparatus for monitoring respiratory condition by impedance pneumography.

BACKGROUND OF THE INVENTION

Impedance pneumography is a known technique of ventilation monitoring, involving the measurement of respiration from electrical impedance changes in the chest. Many investigations have confirmed the high correlation between impedance change and volume of air breathed, whilst the simplicity of this method of respiratory monitoring makes it a very attractive technique as direct contact with the airstream is not required. In practice, the technique is carried out by placing two or four ECG electrodes on the chest wall, and both the electrocardiogram and impedance pneumogram may be recorded from the same electrode set.

Impedance changes, particularly in the chest, are a complex function of geometry and conductivity and many studies have been undertaken in an attempt to understand the relationship between impedance changes and specific physiological changes. In conventional impedance pneumography, little current passes through the lung tissue itself and it is the current passing through the subject's chest and back that contributes most to the impedance change. This is one of the reasons why movement artefact in the resulting pneumogram may be very significant, and in measurements where it is difficult to restrict movement, conventional pnuemographic monitoring can be highly unreliable. In a particular and important application, sleep apnoea detection systems using impedance pneumography techniques give very unsatisfactory results, due to the sensitivity to body movement. Changes in body shape and/or in the skin-to-electrode impedance can produce large amplitude artefacts, in many cases larger than the respiratory signal itself. In neonates and infants especially, the impedance fluctuations caused by cardiac activity can be misclassified as breathing, which might falsely prevent an alarm if obstructive apnea occurs.

A recent investigation into transthoracic impedance, "Signal-to-Motion Artefact Ratio Versus Frequency for Impedance Pneumography", Rosell & Webster, IEEE Transactions on Biomedical Engineering, Vol. 42, No. 3, March 1995, pages 321–323, demonstrated the frequency-dependent aspects of pneumograph measurements. The study described concluded that working at higher frequencies improves the signal-to-motion artefact ratio and suggested a method to further increase this ratio. Development of this study has led to the design and testing of an adaptive filter to increase the signal-to-motion artefact ratio ("Reduction of Motion Artefact Using a Two-Frequency Impedance Plethysmograph and Adaptive Filtering", Rosell, Cohen & Webster, IEEE Transactions on Biomedical Engineering, Vol. 42, No. 10, October 1995, pages 1044–1048).

Other studies into multifrequency impedance monitoring have led to the finding that the amplitude of the transthoracic impedance (measured using a four-electrode system) decreases with frequency ("Multifrequency data collection and modelling of cardiac and respiratory related electrical impedance changes", Brown, Lu, Smallwood & Leathard, in Concerted Action on Electrical Impedance Tomography, Barcelona meeting, UPC, Barcelona 1993).

SUMMARY OF THE INVENTION

The present invention has resulted from studies carried out by the inventor to develop a method of ventilation monitoring less subject to movement artefact and therefore applicable in general patient monitoring, respiratory distress syndrome (RDS) and in sleep studies.

According to a first aspect of the invention, there is provided a method for monitoring respiratory condition by impedance pneumography comprising the steps of applying a first pair of spaced electrodes to a human body, applying a second pair of spaced electrodes for detecting a resulting electrical signal at different points on the body, applying an electrical signal to the first pair of electrodes at a plurality of frequencies, monitoring the resulting electrical signal at the second pair of electrodes at said plurality of frequencies, obtaining from the resulting electrical signal a measure of the impedance of a part of the body at the plurality of frequencies, obtaining a difference signal representing the impedance change with frequency, and dividing the difference signal by a signal representative of the impedance measure itself at one or more frequencies, thereby suppressing the effect of those impedance signal components whose frequency dependent change is substantially proportional to the impedance signal value.

The applied electrical signal is preferably a high frequency constant sinusoidal alternating current of an appropriate magnitude (eg. 100 $\mu$A), whilst the monitored electrical signal is preferably the real part of the resulting potential difference measured over the current path across the second pair of electrodes. As a constant drive current is employed, the impedance measure can be derived directly from the monitored potential difference.

The invention arises from observations by the inventor in electrical impedance tomography which have shown that for a region of interest over the lungs the absolute impedance changes during ventilation generally do not fall with frequency, whereas the impedances themselves do fall with frequency. If movement artefact is simply caused by changes in geometry then this should be represented by an artefact which is a constant fraction of the reference or 'baseline' impedance. It is therefore possible, by making use of the method of the invention, to separate ventilatory changes from movement changes.

The invention differs significantly from the known methods of impedance pneumography, which in no way consider normalising an impedance difference signal with respect to a signal representing the impedance itself.

The difference signal may be divided by a sum of the impedance measure at more than one frequency and this may be a weighted sum, the weighting selected according to appropriate criteria depending, for example, on a presupposed reliability of the measure at the different frequencies, and/or on knowledge of the way the electrical properties of lung tissue respond at different frequencies. For example, the weighting factors may all be zero except for that applied to the impedance measure at the lowest frequency. Preferably the frequencies are in the kHz range.

The signal obtained by the method described above may be low-pass filtered to remove or reduce, amongst other components, cardiac components which may produce unwanted artefact.

Alternatively or additionally, the signal may be band-pass filtered to remove or reduce the DC component of the signal.

In a preferred manner of carrying out the invention, the input electrodes may be situated on opposed sides, left and right, of the subject's trunk whilst the output electrodes may be both placed on one side, preferably the right side, of the subject's trunk. If the output electrode pair is placed on the right side of the subject's trunk, the isolated electrode of the input pair is preferably located in the neighbourhood of the subject's left axilla.

According to a second aspect of the invention, there is provided an apparatus for carrying out the above defined method, comprising a pair of spaced electrodes for applying an electrical signal to a human body and a pair of spaced electrodes for detecting a resulting electrical signal at different points on the body, a means for applying said signal to the first pair of electrodes at a plurality of frequencies, a means for monitoring the resulting electrical signal at the second pair of electrodes at said plurality of frequencies, a means for obtaining from the resulting electrical signal a measure of the impedance of a part of the body at the plurality of frequencies, a means for obtaining a difference signal representing the impedance change with frequency, and a means for dividing the difference signal by a signal representative of the impedance measure itself at one or more frequencies, such that the effect of those impedance signal components whose frequency change is substantially proportional to the impedance signal value can be suppressed.

The means for applying the electrical signal preferably comprises a signal generator capable of producing a plurality of high frequency constant alternating current signals, as well as two flexible leads for connection to the first pair of electrodes. The means for monitoring and/or the means for obtaining the impedance measure may comprise one or more adjustable gain voltage amplifiers, whilst the means for obtaining the difference signal and the means for dividing the difference signal by the signal representative of the impedance measure itself at the one or more frequencies preferably comprises a microprocessor, such as a PC, with a memory such that the signal may be sampled as appropriate and recorded for further processing. The apparatus may further include an output display and/or a printer. The microprocessor may include means for selective filtering of the signal, such as low-pass filtering means and means for dc rejection filtering after the low pass filter.

BRIEF DESCRIPTION OF THE DRAWING

The invention will now be described in more detail with reference to the accompanying drawings, in which.

ELECTRODE PLATING

Figure 1:
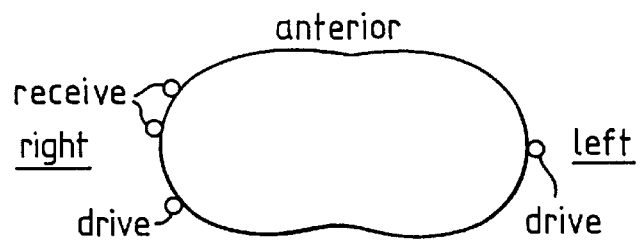
FIG. 1 depicts electrode placement in relation to the body including a drive electrode and receive electrodes.

The studies used a tetrapolar electrode arrangement, since such an arrangement minimises the effect of contact impedance changes on the impedance measured. It was necessary to devise an electrode placement which maximised the contribution of both lungs to the measurement, and this optimum placement was identified by inspecting all the data collected from a conventional 16 electrode EIT system and looking for the electrode combination which maximised the fractional impedance change during respiration. This optimised electrode placement was found to be an isolated drive electrode at the left axilla, whilst the other drive electrode and the two receive electrodes were placed in close proximity to one another on the right side of the body, all three in approximately the same transverse plane at about the level of the 6th or 7th rib. The receive electrodes were spaced by about 5 cm, whilst the second drive electrode was placed about 10 cm further to the rear. FIG. 1 depicts diagrammatically this arrangement. Clearly alternative electrode positions may be employed, such as those selected to target the impedance change originating in only the left or only the right lung. None of the electrodes need be arranged in a common transverse plane, and a 3-d arrangement may be used as required to highlight the impedance change associated with a particular target region. Additionally, the invention may be realised using more than four electrodes.

EXPERIMENTAL PROCEDURE

A signal generator capable of providing sinusoidally varying current of constant 1 mA peak-to-peak amplitude simultaneously at different frequencies was used to supply the electrical signal to the drive electrodes. The drive signal was applied to normal male subjects at number of different frequencies, including 9.6 kHz, 38.4 kHz and 76.8 kHz, with the electrode placing specified above. Sample results are illustrated in FIGS. 2–5 and show the real part only of the impedance measured against time in seconds from the beginning of the respective test. The results were high-pass filtered to remove or at least reduce the cardiac signal.

Figure 2:
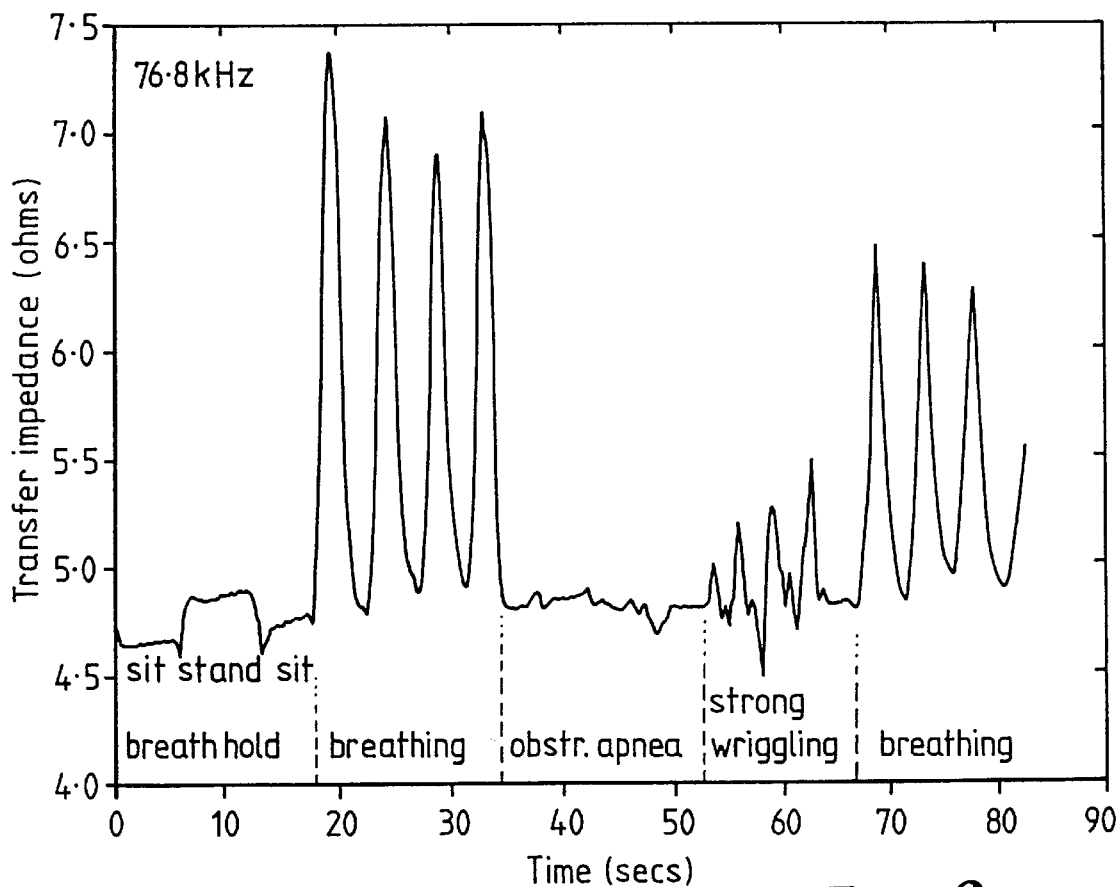
FIG. 2 shows a graph of the transfer impedance in ohms at a frequency of 76.8 kHz during maneuvers carried over a 90 second period.

In FIG. 2, the transfer impedance in ohms at a frequency of 76.8 kHz is shown during various manoeuvres carried over a 90 second period. The "strong wriggling" consisted of twisting the trunk backwards, forwards and sideways as much as possible. During the initial period of breath-hold the subject also changed from sitting to a standing position and then back again. The breathing periods involved deep breathing, from maximum inspiration to maximum exhalation, and it can be seen that the changes in transfer impedance with breathing as a fraction of baseline (~45%) are very large. The "obstructive apnoea" period was simulated by applying a noseclip to the patient and having him close his mouth whilst still attempting to breathe using the muscles of the diaphragm and abdomen. The impedance changes here therefore represent respiratory effort rather than ventilation.

Figure 3:
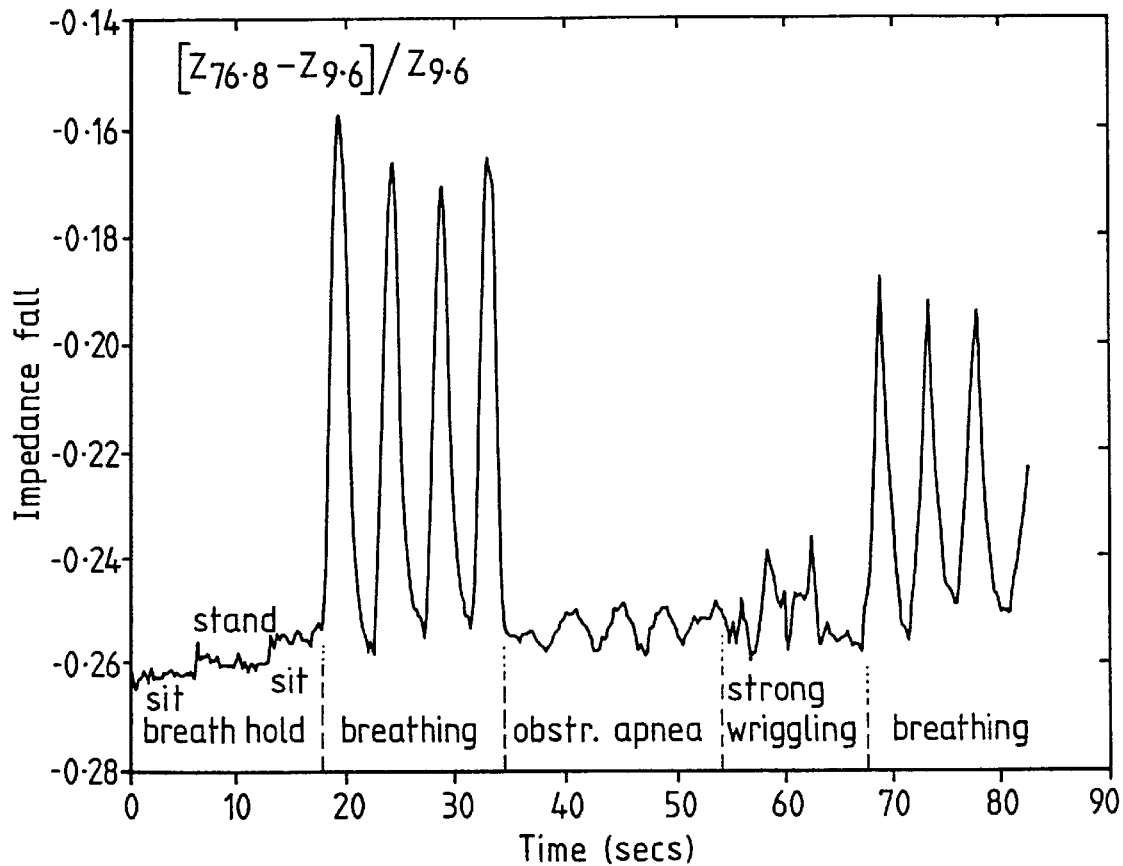
FIG. 3 shows the same data as FIG. 2 but this time presented by reference to the 9.6 kHz data.

In FIG. 3 the same data is shown, but this time presented by reference to the 9.6 kHz data. The vertical scale therefore shows the (non-dimensional) fractional fall in impedance with frequency. The low frequency was chosen as the reference impedance because it is understood that low frequency impedance measurements are often the most accurate. The improvement in discrimination of ventilatory changes and movement changes is clear, particularly in the case of the significant change in impedance between sitting and standing, which discontinuity is largely suppressed by making use of the method of the invention.

Figure 4A:
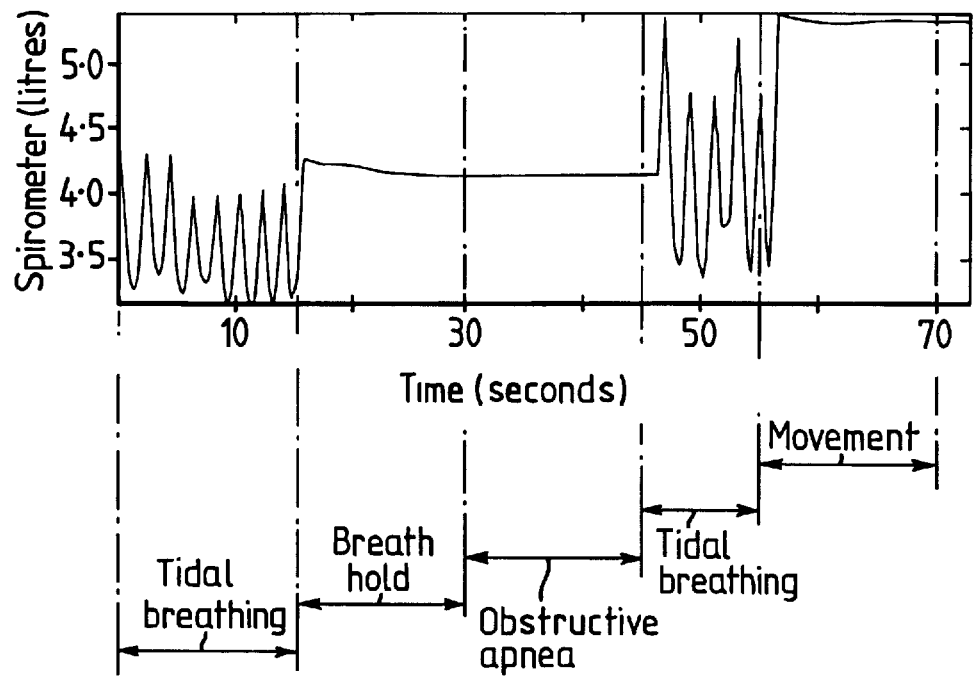
FIGS. 4a–4c show three traces recorded simultaneously from a measurement period consisting of various movements.
Figure 4B:
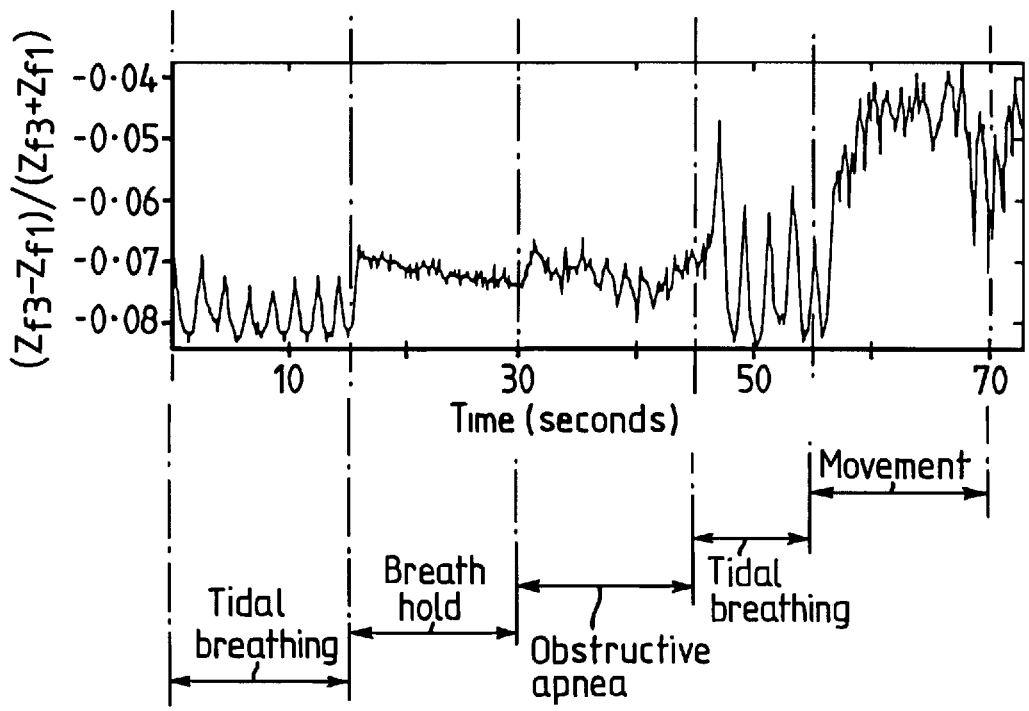
Figure 4C:
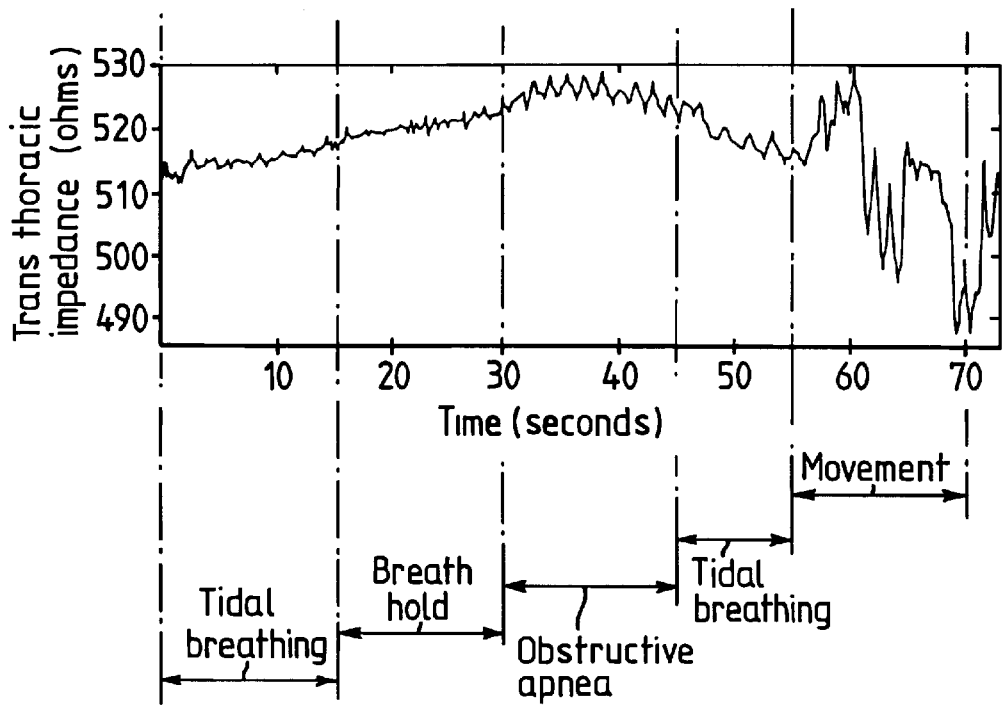

FIGS. 4a–c show three traces recorded simultaneously from a measurement period consisting of various movements. The 'tidal breathing' referred to in these figures was ordinary, fairly shallow breathing, and the movement period involved strong wriggling by the subject. FIG. 4a shows the trace from an airflow spirometer (a Gould water-sealed bell spirometer), whilst FIG. 4b shows the impedance change data presented with reference to a 'baseline' impedance, $(Z_{f3}-Z_{f1})/(Z_{f3}+Z_{f1})$. The 'baseline' impedance of $(Z_{f3}+Z_{f1})$ was selected here to reference the impedance change over a broader frequency range than that used in the case of the results shown in FIG. 3. f1 and f3 were, respectively, 9.6 kHz and 38.4 kHz. FIG. 4c shows the transthoracic impedance, recorded as a bipolar impedance measurement between the two drive electrodes. Comparison of the traces clearly shows the significance of employing the method according to the invention, especially when compared with the simple bipolar pneumogram which gives very poor discrimination. Movement artefact is still evident in the trace of FIG. 4b, but it is of considerably lower magnitude than respiratory changes. The normalisation of the results with reference to the sum of the impedance measures at two frequencies appears to give improved movement artefact suppression. It is also possible to normalise the results using a sum of the measures at more than two frequencies, or by making use of a weighted sum of impedance measures at the different frequencies, the weighting factors being selected according to presupposed characteristics. For example, the weighting may take into account the presupposed reliability of the measure at the different frequencies, or may be selected according to knowledge of the way lung tissue behaves at different frequencies.

Figure 5A:
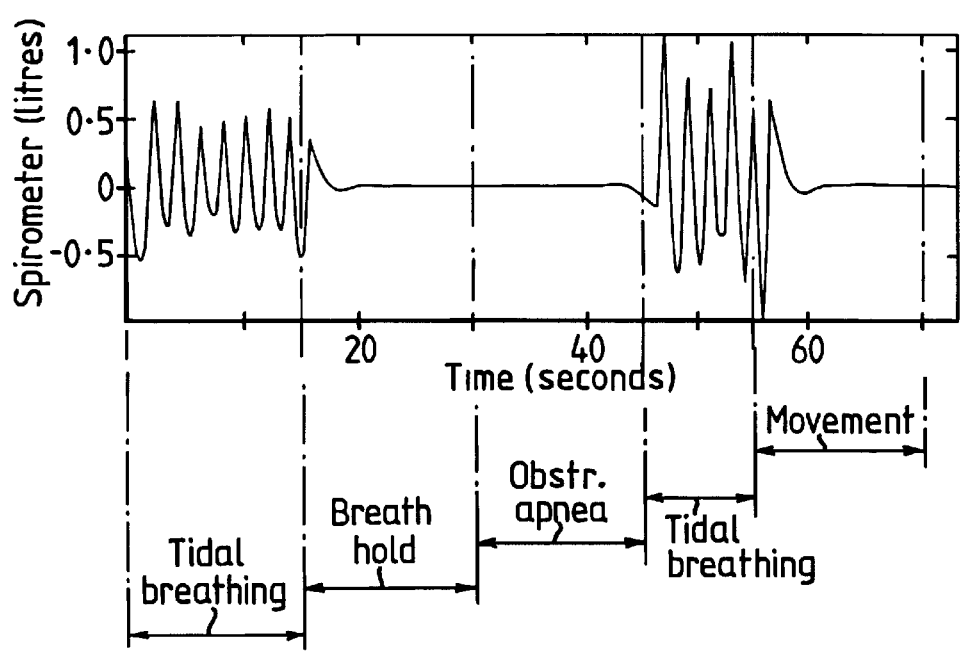
FIGS. 5a–5c show the traces of FIGS. 4a–4c which have been band-pass filtered from 0.125 to 2.5 Hz.
Figure 5B:
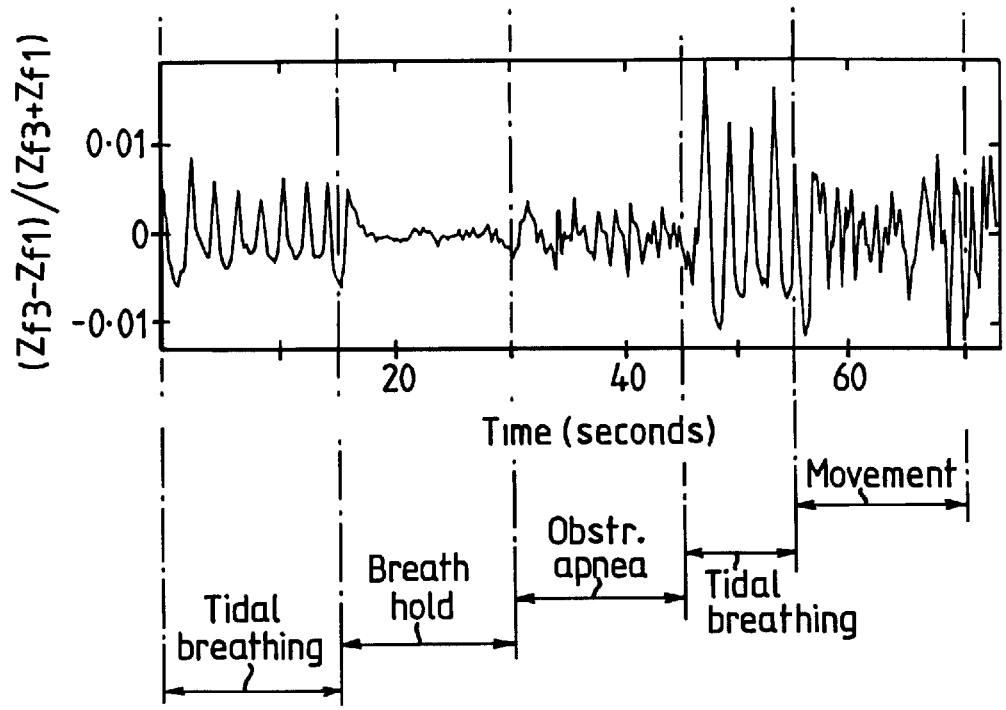
Figure 5C:
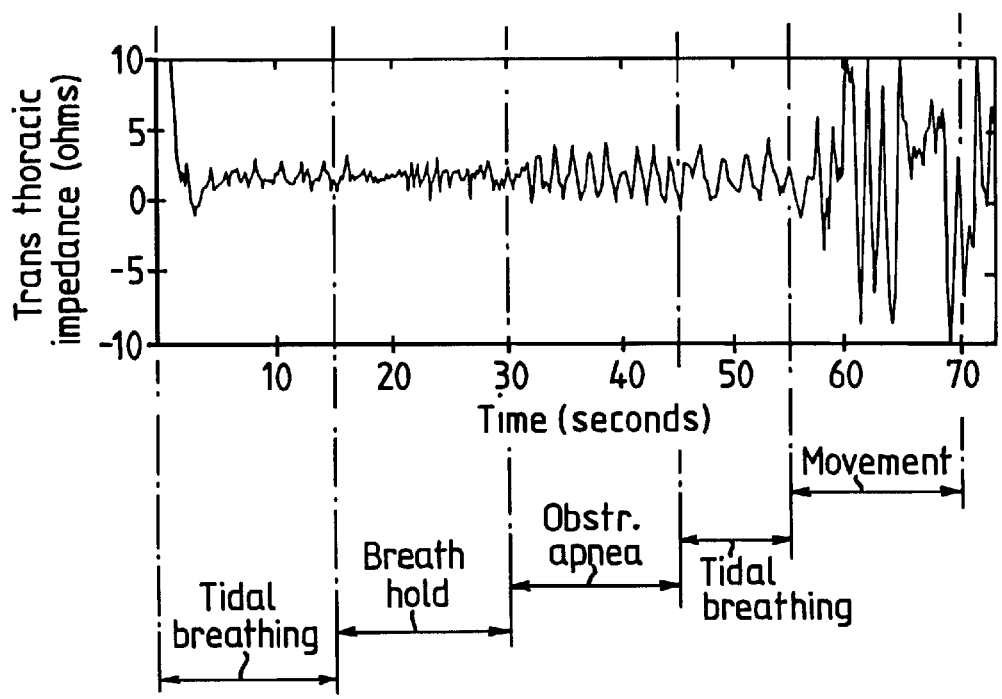

Finally, FIGS. 5a to 5c show the traces of FIGS. 4a to 4c, but in this case all three traces have been band-pass filtered from 0.125 to 2.5 Hz. This has the effect of removing the DC component of the signal. With such filtering, results from the conventional transthoracic impedance measurement (FIG. 5c) shows some improvement, but it is clear that the trace resulting from the method of the invention (FIG. 5b) provides a much clearer correlation with that derived from the airflow spirometer.

Embodiments of the invention described above are given by way of example only, and it should be understood that these in no way limit the invention which is intended to embrace all embodiments that fall within the scope of the appended claims.

I claim:

1. A method for monitoring respiratory condition by impedance pneumography, comprising the steps of applying a first pair of spaced electrodes to a human body, applying a second pair of spaced electrodes for detecting a resulting electrical signal at different points on the body, applying an electrical signal to the first pair of electrodes at a plurality of frequencies, monitoring the resulting electrical signal at the second pair of electrodes at said plurality of frequencies, obtaining from the resulting electrical signal a measure of the impedance of a part of the body at the plurality of frequencies, obtaining a difference signal representing the impedance change with frequency, and dividing the difference signal by a signal representative of the impedance measure itself at one or more frequencies, thereby suppressing the effect of those impedance signal components whose frequency dependent change is substantially proportional to the impedance signal value.

2. A method according to claim 1, wherein the applied electrical signal is a high frequency constant sinusoidal alternating current.

3. A method according to claim 1, wherein the monitored electrical signal is the real part of the resulting potential difference measured over the current path across the second pair of electrodes.

4. A method according to claim 1, wherein the difference signal is divided by a sum of the impedance measures at more than one frequency.

5. A method according to claim 4, wherein said sum of the impedance measures is a weighted sum.

6. A method according to claim 5, wherein the weighting is selected according to a presupposed reliability of the measure at the different frequencies.

7. A method according to claim 1, wherein the plurality of frequencies are in the kHz range.

8. A method according to claim 1, wherein the resulting electrical signal is passed through a low-pass filter.

9. A method according to claim 1, wherein the resulting electrical signal is band-pass filtered to remove or reduce the DC component of the signal.

10. A method according to claim 1, wherein the input electrodes are situated on opposed sides of the subject's trunk, whilst the output electrodes are both placed on one side of the subject's trunk.

11. An apparatus for monitoring respiratory condition by impedance pneumography, comprising a pair of spaced electrodes for applying an electrical signal to a human body and a pair of spaced electrodes for detecting a resulting electrical signal at different points on the body, a means for applying said signal to the first pair of electrodes at a plurality of frequencies, a means for monitoring the resulting electrical signal at the second pair of electrodes at said plurality of frequencies, a means for obtaining from the resulting electrical signal a measure of the impedance of a part of the body at the plurality of frequencies, a means for obtaining a difference signal representing the impedance change with frequency, and a means for dividing the difference signal by a signal representative of the impedance measure itself at one or more frequencies, such that the effect of those impedance signal components whose frequency change is substantially proportional to the impedance signal value can be suppressed.

12. An apparatus according to claim 11, wherein the means for applying the electrical signal comprises a signal generator for producing simultaneously a plurality of high frequency constant alternating current signals, and connection means for supplying such signals to the first pair of electrodes.

13. An apparatus according to claim 11, wherein the means for monitoring the resulting electrical signal includes at least one adjustable gain voltage amplifier.

14. An apparatus according to claim 11, wherein the means for obtaining the difference signal and the means for dividing the difference signal by the signal representative of the impedance measure itself at the one or more frequencies comprises a microprocessor computing means.

15. An apparatus according to claim 14, wherein the microprocessor computing means includes means for low-pass filtering of the resulting electrical signal.

16. An apparatus according to claim 14, wherein the microprocessor means includes means for dc rejection filtering.

17. An apparatus for monitoring a respiratory condition by impedance pneumography, comprising:
- a pair of spaced electrodes for applying an electrical signal to a human body;
- a pair of spaced electrodes for detecting a resulting electrical signal at different points on the body;
- a signal generating device for applying said electrical signal to the first pair of electrodes at a plurality of frequencies;
- a monitoring device for monitoring the resulting electrical signal at the second pair of electrodes at said plurality of frequencies;
- a computing device for obtaining from the resulting electrical signal a measure of the impedance of a part of the body at the plurality of frequencies;

a computing device for obtaining a difference signal representing the impedence change with frequency;

a computing device for dividing the difference signal by a signal representative of the impedence measure itself at one or more frequencies, whereby the effect of those impedence signal components whose frequency is substantially proportional to the impedence signal value can be suppressed.

* * * * *